United States Patent [19]

Sommer

[11] Patent Number: 4,917,496

[45] Date of Patent: Apr. 17, 1990

[54] PARTICLE SIZE MEASURING INSTRUMENT WITH DIRECT SCATTERED LIGHT DETECTION

[75] Inventor: Holger T. Sommer, Greenbelt, Md.

[73] Assignee: Pacific Scientific Company, Anaheim, Calif.

[21] Appl. No.: 217,337

[22] Filed: Jul. 11, 1988

[51] Int. Cl.⁴ ............................................. G01N 15/02
[52] U.S. Cl. .................................... 356/336; 356/338; 250/574
[58] Field of Search ............... 356/336, 338, 337, 335, 356/340; 250/574, 564, 576

[56] References Cited

U.S. PATENT DOCUMENTS

| | | |
|---|---|---|
| 3,200,700 | 8/1965 | Topol . |
| 3,680,962 | 8/1972 | Hayakawa . |
| 3,770,351 | 11/1973 | Wyatt . |
| 4,320,978 | 3/1982 | Sato . |
| 4,361,403 | 11/1982 | Loos ..................................... 356/336 |
| 4,387,993 | 6/1983 | Adrian ................................. 356/336 |
| 4,492,467 | 1/1985 | Drain et al. .......................... 356/336 |
| 4,507,556 | 3/1985 | Brenholdt . |
| 4,690,560 | 9/1987 | Coogan . |
| 4,772,126 | 9/1988 | Allemand et al. ................... 356/336 |
| 4,801,205 | 1/1989 | Tatsuno ............................... 356/336 |
| 4,830,494 | 5/1989 | Ishikawa et al. .................... 356/336 |

Primary Examiner—Léon Scott, Jr.
Attorney, Agent, or Firm—Lane & Aitken

[57] ABSTRACT

In an instrument for measuring the size of particles entrained in a fluid stream, photodetectors are mounted on the walls of tubing shaping the flow of the fluid stream through a laser beam. The photodetectors generate electric current pulses in response to scattering of the light which is generated by the particles passing through the laser beam. The pulses generated by the photodetectors provide a measurement of particle size. The photodetectors are mounted either adjacent to the laser beam on the tubing walls or, alternatively, the tubing walls are mirrored above and below the laser beam and the photodetectors are mounted on the tubing walls at right angle bends of the tubing to receive the light reflected from the mirrored surfaces.

12 Claims, 4 Drawing Sheets

PARTICLE SIZE MEASURING INSTRUMENT WITH DIRECT SCATTERED LIGHT DETECTION

This invention relates to an instrument for measuring particle sizes entrained in a fluid stream and, more particularly, to an instrument which measures particle sizes by light scattering from the particles as the particles pass through a beam of light directed through the stream in which the particles are entrained.

BACKGROUND OF THE INVENTION

In copending application Ser. No. 144,225, filed Jan. 15, 1988, invented by Kenneth Paul VonBargen, and assigned to the assignee of this application, there is disclosed a particle measuring instrument of the general type to which the present invention is directed. As disclosed in the above-identified copending application, particles entrained in a fluid are measured by passing a beam of light through the fluid stream, detecting the resulting light forward scattered from particles passing through the light beam to generate pulses and determining the amplitude and the length of the resulting pulses as measurements of the particle sizes.

SUMMARY OF THE INVENTION

The present invention is an improvement in the instrument of the above-described application in that it provides a more efficient method of detecting the light scattered from particles passing through a shaped light beam, which in the preferred embodiment is a laser beam. In accordance with the invention, instead of detecting the light forward scattered from particles passing through the light beam, photodetectors are mounted on the wall of the tubing which shapes the flow of the stream passing through the light beam. In accordance with one embodiment of the invention, the tubing extending away from the middle of the measurement cell is transparent and photodetectors surround the transparent tube immediately above and below the laser beam. In accordance with another embodiment of the invention, mirrored surfaces are provided on the walls of the tubing immediately above and below the laser beam to reflect the light to photodetectors mounted on the wall of the tubing where the tubing is formed into right angle bends. With these arrangements, more of the light scattered from particles passing through the laser beam is collected directly on the surfaces of the photodetectors and, thus, the scattered light is detected more efficiently than in the instrument described in the above-mentioned copending application, or in other particle measuring instruments which measure particle size by light scattered from entrained particles.

DESCRIPTION OF THE PREFERRED EMBODIMENTS

Figure 1:
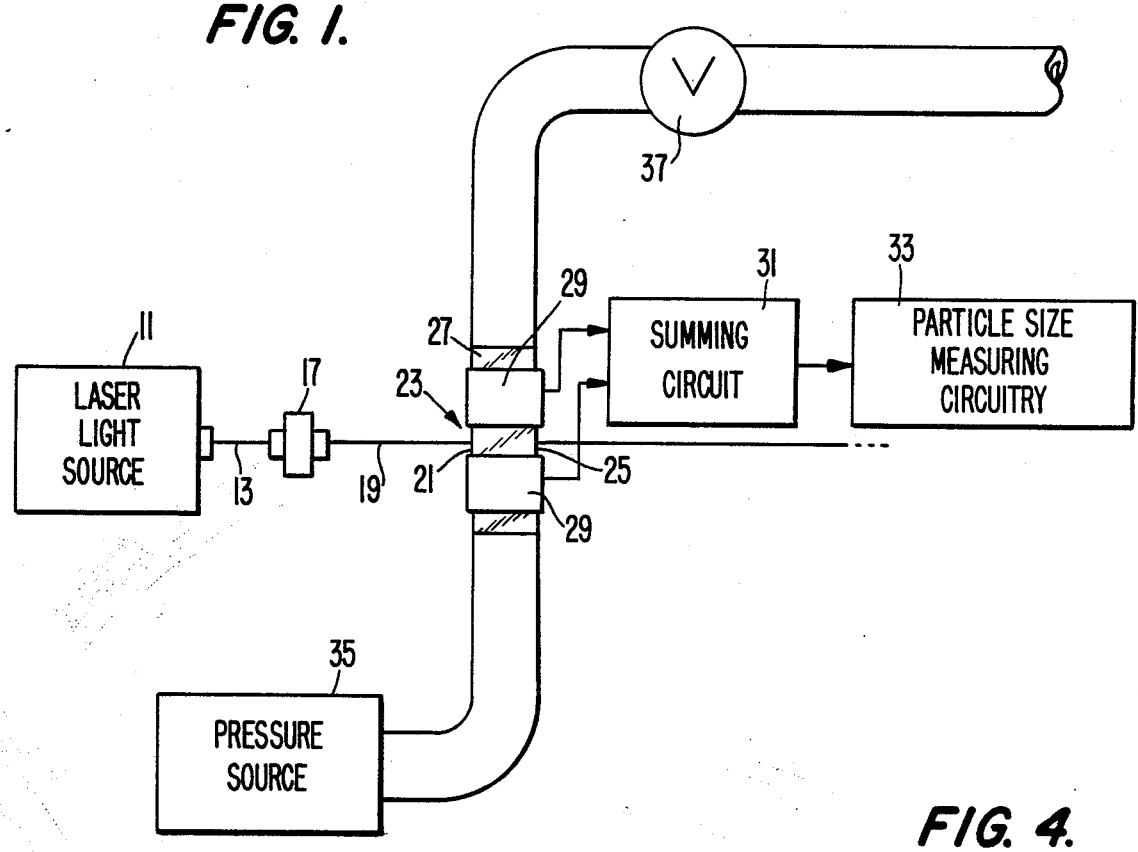
FIG. 1 schematically illustrates a particle size measuring instrument in accordance with the present invention.

As shown in FIG. 1, in the instrument of the invention, a laser 11 generates a collimated laser beam 13, which is directed through to a beam expander 17. The beam 17 shapes the received laser beam into the form of a thin, flat sheet 19, which in the preferred embodiment, is 1 millimeter wide and 35 microns thick. The flat, sheet-like beam is transmitted through a transparent window 21 of a measuring cell 23, which is arranged to have a sample stream of fluid to be tested, flowing through the laser beam. The plane of the flat shape of the beam is perpendicular to the direction of fluid flow. In the specific embodiments, the fluid is liquid, but the invention is also applicable to measuring the size of particles entrained in gases. Also, in the specific embodiment shown in FIG. 1, the direction of flow is upward through the laser beam, but the cell may be oriented to have the flow in any direction. The laser beam is adapted to uniformly illuminate the cross section of the fluid passageway for carrying the fluid stream through the laser beam. The laser beam, passing through the fluid stream in the cell 23, exits from the cell through an exit window 25 of the measuring cell. The laser light 19, encountering any particles in the fluid flowing through the cell 23, will be partially scattered by such particles. The cell 23 includes a transparent tube 27 extending vertically in both directions from the middle of the cell where the laser beam passes through the cell. The transparent tube 27 is surrounded by and has mounted on the tube walls photodetectors 29. The light scattered by particles passing through the laser beam is detected by the photodetectors 29, which convert the impinging scattered light rays into pulses. The pulses from the photodetectors 29 are summed in a summing circuit 31 into unitary pulses so that one pulses is produced for each particle and the pulses are applied to particle size measuring circuitry 33. The fluid entraining the particles to be measured is caused to flow through the cell 23 by means of a pressure source 35. Downstream of the cell is a valve 37, which controls the rat of flow through the cell 23 to be at a constant rate. The particle size measuring circuitry 33 measures particle sizes by the amplitude and width of pulses in the same manner as described in the above-described copending application Ser. No. 144,225.

Figure 2:
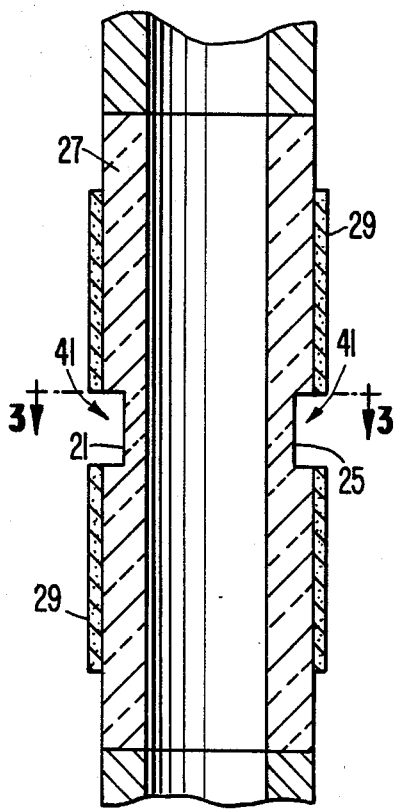
FIG. 2 is an enlarged sectional view in elevation taken through the measuring cell of the instrument in accordance with one embodiment of the invention.
Figure 3:
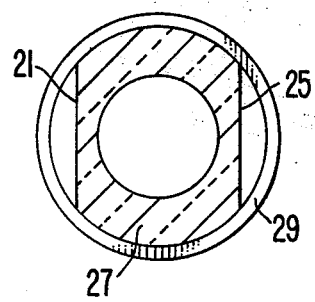
FIG. 3 is a cross-sectional view taken along the line 3—3 in FIG. 2.
Figure 4:
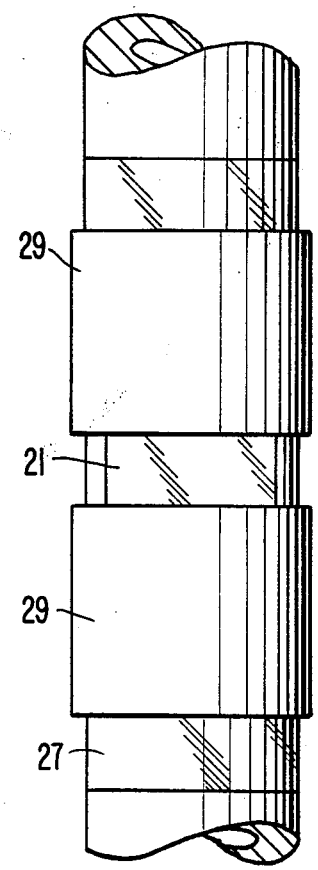
FIG. 4 is a side view in elevation of the measuring cell shown in FIG. 2.

In the embodiment of the invention illustrated in FIGS. 2-4, the transparent tube 27 of the detecting cell 23 is round and has a round interior channel 1.5 millimeters in diameter. The round tubing at the center of the cell is formed with flat faces to define the entrance window 21 and the exit window 25 for the laser beam passing through the middle of the cell. The flat surfaces of the window 21 and 25 are formed by grooves 41 cut into the cylindrical wall of the tube 27. The grooves 41 are 0.5 millimeters wide measured from top to bottom as shown in FIG. 2. The photodetectors 29 are cylindrical, completely surround the transparent tube 27, and extend upwardly and downwardly from the edges of the grooves 41. The photodetectors are formed on the cylindrical tube 27 by depositing amorphous silicon directly on the tube 27. The photodetectors 29 have an internal cylindrical photosensitive surface surrounding the fluid stream and operate in the photovoltaic mode to detect light impinging on the photosensitive surface.

Additional photodetectors could also be deposited on the exterior tube wall on the sides of the tube between the grooves 41 to collect more of the light scattered from the laser beam by particles passing through the laser beam.

Figure 5:
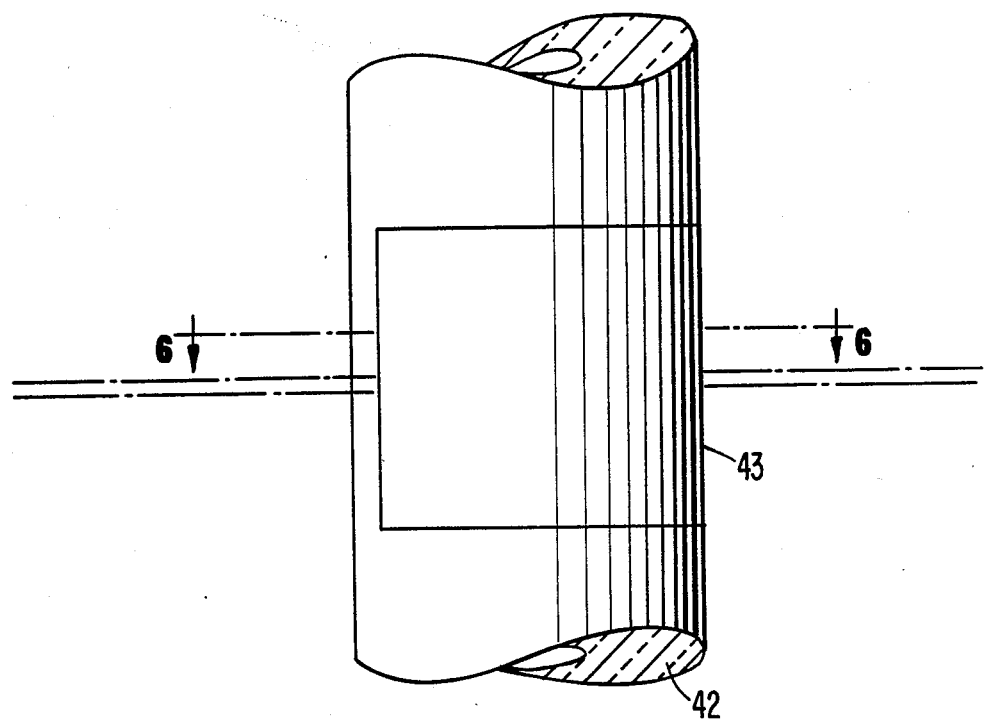
FIG. 5 is a side view in elevation of a measuring cell of the instrument in accordance with another embodiment of the invention.
Figure 6:
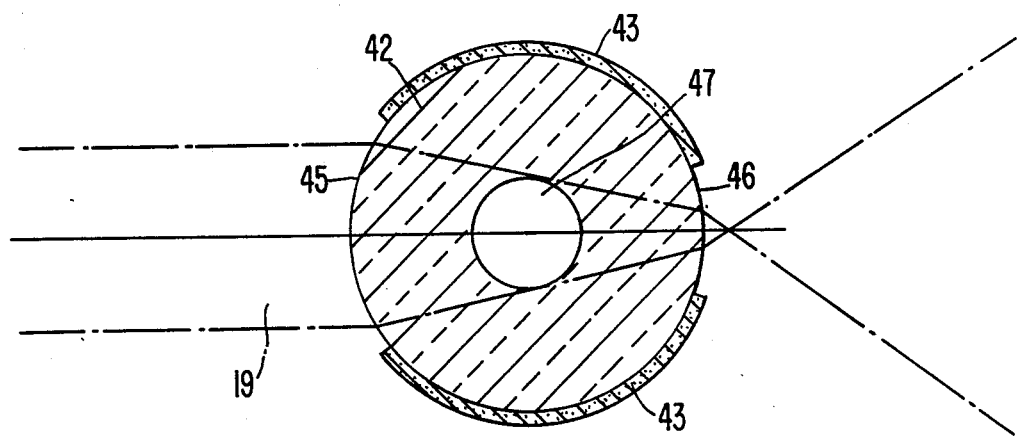
FIG. 6 is a cross sectional view of the measuring cell of FIG. 5 taken along the line 6—6.

The measurement cell shown in FIGS. 5 and 6, as in the embodiment of FIGS. 2 through 5, comprises a round transparent tube 42 in which photodetectors in the form of cylindrical segments 43 are formed on opposite sides of the tube at the center of the cell each extending over an angle of 122 degrees. The photodetectors leave a gap of 44 degrees on one side of the tube to define an entrance window 45 for the laser beam and a gap of 40 degrees on the opposite side of the tube to define an exit window 46 for the laser beam. As shown in FIG. 6, the laser beam 19 encountering the cylindrical face of the entrance window 45 will be focused upon passing through this cylindrical surface toward the cylindrical passage way 47 through which the fluid entraining the particles passes. The focusing provided by the arcuate face of the window 45 contracts the laser beam by an amount just to coincide with the size of the cylindrical passage way. In this manner, the laser beam 19 is concentrated by the focusing effect of the cylindrical face 45 to just fill the cross-section of the passageway 47 with the laser beam and so that the intensity of the laser beam encountered by the particles is intensified.

As in the embodiments of FIGS. 2 through 4, the photodetectors 43 will detect light scattered from particles in the fluid stream passing through the laser beam 45 and generate an electrical pulse in response to each particle. If desired, additional photodetectors can be formed on the walls of the tube above and below the laser beam 45 in the gaps between the photodetectors 43 so as to collect additional scattered light from the particles.

The embodiments of FIGS. 2-6 have the advantage of using round tubing. However, the detecting cell of these embodiments have the disadvantage of the difficulty of forming the photodetectors on the cylindrical tubing.

Figure 9:
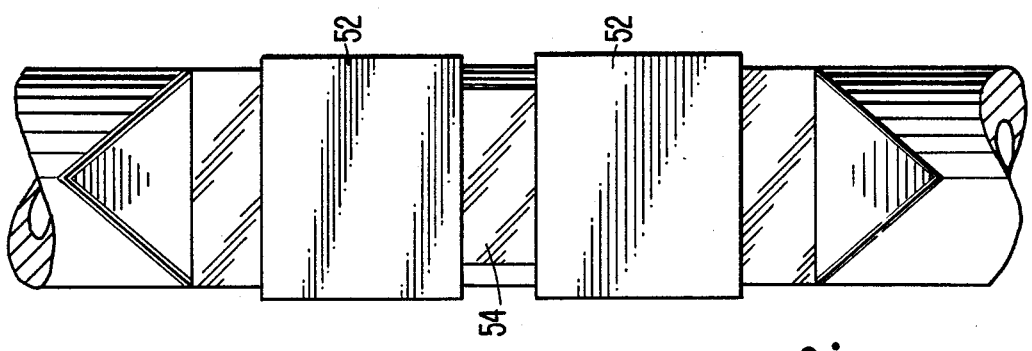
FIG. 9 is a side view in elevation of the measuring cell shown in FIG. 7.
Figure 7:
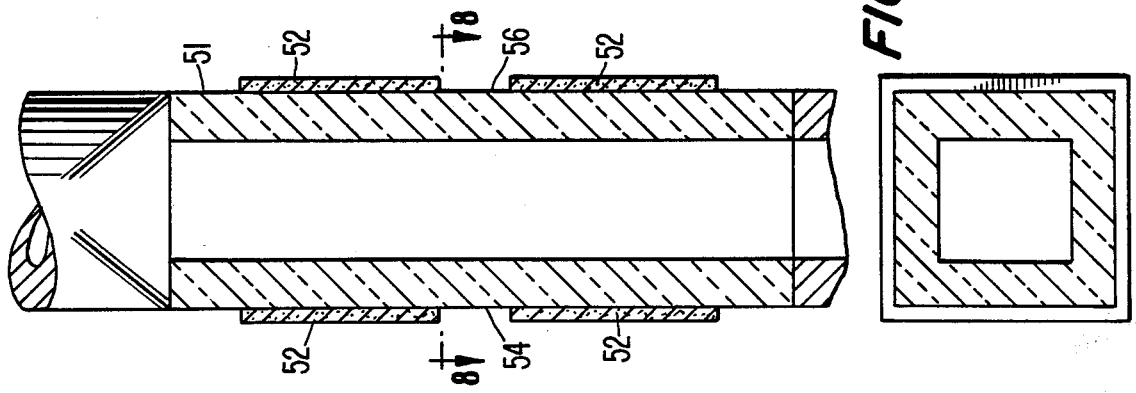
FIG. 7 is an enlarged sectional view in elevation of the measuring cell of the instrument in accordance with another embodiment of the invention.
Figure 8:
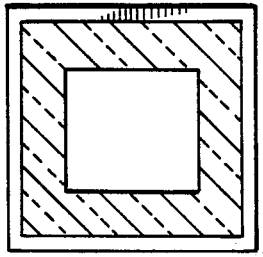
FIG. 8 is a cross-sectional view taken along the line 8—8 of FIG. 7.

In the embodiment of FIGS. 7-9, the particle detecting cell is similar to that of FIGS. 2-6 except that the transparent tube of the cell, designated by reference number 51, is rectangular instead of round. Accordingly, instead of having a cylindrically shaped photodetecting cell formed on the transparent tube, the photodetecting cells comprise eight rectangular PIN photodiodes 52, four of them mounted on the rectangular walls directly above the laser beam and four of the cells mounted directly on the walls below the laser beam surrounding the rectangular tubing above and below the laser beam. The photosensitive surfaces of the photodiodes 52 face and surround the fluid stream. The photodiodes on the front and rear faces of the rectangular tube are spaced apart by 0.5 millimeters to define an entrance window 54 and an exit window 56 for the laser beam to enter the cell and exit from the cell. The rectangular tube's exterior dimension is 3 millimeters square and the rectangular channel within the cell has an interior dimension of 1.3 millimeters on each side.

Because the photodetectors are rectangular, they do not have to be formed by being deposited on the tubing wall, but can be mounted on the tubing wall by means of a transparent adhesive. Thus, conventional semiconductor photodiodes may be used.

Figure 10:
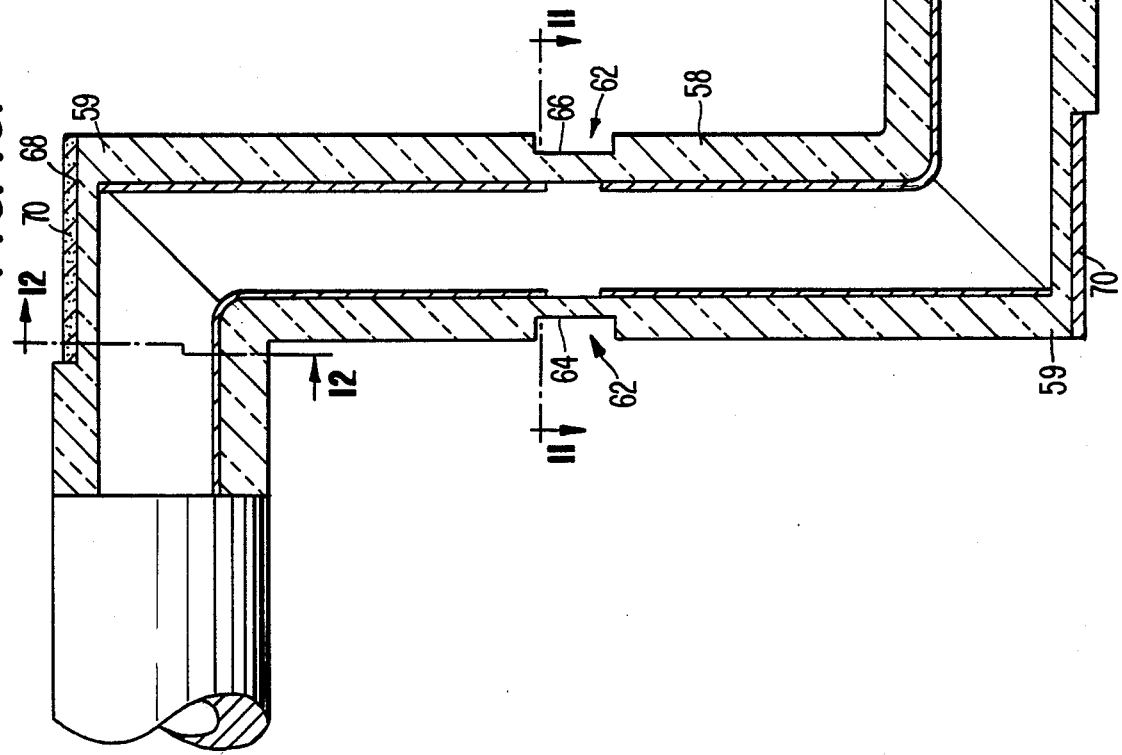
FIG. 10 is an enlarged sectional view in elevation of the measuring cell of the instrument in accordance with another embodiment of the invention.
Figure 11:
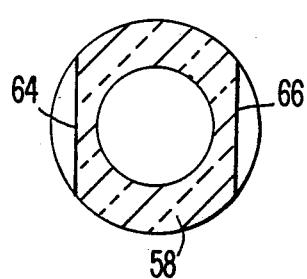
FIG. 11 is a cross-sectional view taken along the line 11—11 of the measuring cell as shown in FIG. 10.
Figure 12:
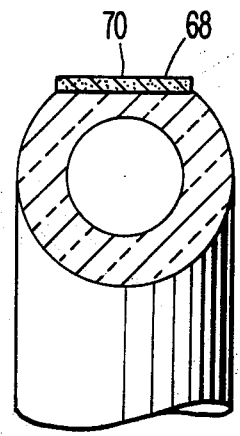
FIG. 12 is a sectional view taken along the line 12—12 through the measuring cell as shown in FIG. 10.

In the embodiment of the particle measuring cell shown in FIGS. 10-12, the tubing 58 of the cell, which is round, is formed into right angle bends 59 at its upper and lower ends to define horizontal sections of the cell. In the center of the cell, grooves 62 are formed 0.5 millimeters wide in the exterior cylindrical wall of the cell to define the flat faces 64 and 66 for the entrance and exit windows of the cell and through which the laser beam is directed.

The interior wall surfaces of the vertical portion of the tubing 58, that is, the portions extending vertically from the center of the cell where the grooves are formed, are mirrored with a specularly reflecting coating 67. The coating 67 extends up and down to the point where the tubing makes the right angle bends 59. At each right angle bend 59, a flat 68 is formed in the exterior wall of the tube directly in line with the axis of the vertical portion of the tube. These flats 68 extend from the corner of the tube to beyond the cylindrical locus of the exterior opposite vertical wall of the tube, so that the flats 68 overlap the entire cylindrical locus of the mirrored surfaces. Mounted on and fully coextensive with the flats are PIN photodiodes 70. The photosensitive surfaces of the photodiodes 70 face the fluid stream and are adjacent to the internal wall of the tube that shapes flow of the fluid stream. The tubing of the cell conveniently is made out of glass and may be transparent throughout its length. However, it is only necessary for the tubing in this embodiment to be transparent opposite the entrance and exit windows 64 and 66 and opposite the photodiodes 70.

Instead of providing the mirrored surfaces on the internal walls of the tubing, the mirrored surfaces may also be provided on the exterior walls in which case the vertical portions of the tubing would have to be transparent instead of employing flats for the entrance and exit windows, the exterior surface of the tube can be left round to achieve a focusing effect, like the embodiment of FIGS. 5 and 6 to concentrate the laser beam in the fluid passageway of the cell.

When a laser beam encounters a particle in the center of the cell shown in FIGS. 10-12 and causes light to be scattered from such particle, the scattered light will be reflected one or more times from the specular coating 67 of the cell and be directed on the photodiodes 70 whereupon the scattered light will be detected and converted into electric pulses.

Figure 13:
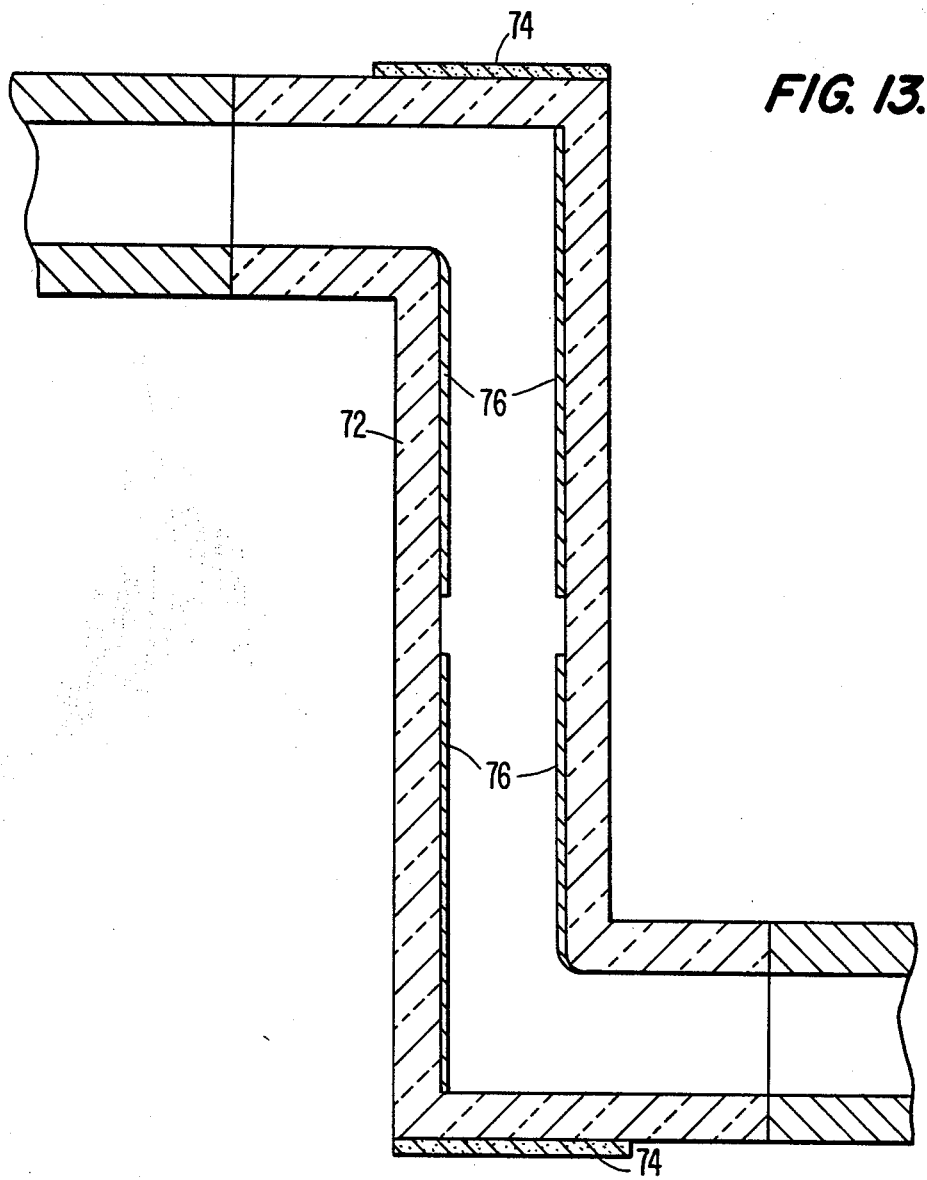
FIG. 13 is an enlarged sectional view in elevation of the measuring cell of the instrument in accordance with another embodiment of the invention.

The embodiment of the particle detecting cell shown in FIG. 13 is like that shown in FIGS. 10-12, except that the tubing 72 of the cell, instead of being round, is rectangular. As a result, no grooves are defined in the wall of the cell to define flat windows for the cell and no flats need to be provided in the wall of the cell where the tube bends. Instead, PIN photodiodes 74 are mounted directly on the exterior flat surfaces of the cell where the tube makes right angle bends with the photodiode extending from sidewall to sidewall of the tube and from the corner of the tube to a point beyond the locus of the vertical extension of the opposite exterior wall of the tube, so that the photodiodes 74 overlap the locus of the rectangular mirrored surface provided by the specular coating 76 of the tube on the interior channel of the tube on all four sides. In this embodiment, the specular coating 76 of the tube will reflect the scattered light to the photodiodes 74 as in the embodiment of FIGS. 10-12. Also in this embodiment, the mirrored surfaces may be formed on the external surface of the tube instead of the internal surface. As in the embodiment of FIGS. 10-12, the tubing is transparent and conveniently may be made out of glass.

In each of the above described embodiments, the light scattered from a particle passing through the laser beam is very efficiently collected by the photodetectors, because essentially almost all of the light scattered from each particle, except for a small portion backwards scattered out of the entrance window or forward scattered out of the exit window, is collected by the photovoltaic cells. As a result, the cells generate relatively high amplitude pulses in response to the light scattered from a given particle and enables the particle sizes to be discriminated with the greater degree of accuracy. Also the need for lenses to collect the scattered light and focus it on a photodetector is eliminated.

The above description is of preferred embodiments of the invention and modification may be made thereto without departing from the spirit and scope of the invention, which is defined in the appended claims.

What is claimed is:

1. A particle measuring system comprising a tube, means to cause fluid entraining particles to be measured to pass through said tube in a fluid stream, said tube having an interior wall surface shaping the flow of said stream, means to direct a shaped beam of light through said stream in said tube perpendicular to the direction of flow of said stream, and at least one photodetector having a photosensitive surface mounted on the wall of said tube with said photosensitive surface positioned adjacent to said interior wall surface and arranged to detect the light scattered from said beam of light by particles in said stream passing through said beam of light.

2. A particle measuring instrument as recited in claim 1, wherein said photodetector is mounted on the wall of said tube to position said photosensitive surface adjacent to said light beam as it passes through said fluid stream.

3. A particle measuring instrument as recited in claim 2, wherein said tube is transparent, said photodetector is mounted on the outside wall of said tube with said photosensitive surface facing said fluid stream.

4. A particle measuring instrument as recited in claim 2, wherein said photosensitive surface surrounds said stream adjacent to said light beam passing through said tube.

5. A particle measuring instrument as recited in claim 2, wherein said tube is rectangular in cross-section.

6. A particle measuring instrument as recited in claim 2, wherein said tube is round and said photosensitive surface is cylindrical.

7. A particle measuring instrument as recited in claim 6, wherein a second photodetector is mounted on the wall of said tube having a cylindrical photosensitive surface facing said stream adjacent said light beam passing through said stream, said light beam passing through the walls of said tube between said photodetectors.

8. A particle measuring instrument as recited in claim 7, wherein said tube has flat surfaces defined in the exterior wall of said tube between said photodetectors, said light beam passing through said flat surfaces.

9. A particle measuring instrument as recited in claim 1, wherein said tube has a right angle bend, and wherein a mirrored surface is formed on the wall of said tube adapted to reflect light scattered from said beam light by particles in said stream, said mirrored surface extending from a location adjacent said beam of light passing through said stream to said right angle bend, said photodetector being mounted on the wall of said tube with said photosensitive surface positioned to receive the light scattered from said beam and reflected by said mirrored surface.

10. A particle measuring instrument as recited in claim 1, wherein said tube is round defining a cylindrical surface through which said beam of light passes to enter said stream, said cylindrical surface focusing said beam to concentrate said beam in said stream.

11. A particle measuring instrument as recited in claim 10, wherein said photodetector is mounted on the exterior wall of said tube and wherein the wall of said tube is transparent adjacent to said photosensitive surface.

12. A particle measuring instrument as recited in claim 10, wherein said photodetector is mounted on the wall of said tube to position said photosensitive surface adjacent to said light beam as it passes through said fluid stream, and a second photodetector is mounted on the wall of said tube opposite said first mentioned photodetector and having a photosensitive surface facing the photosensitive surface of said first photodetector, said cylindrical external surface of said tube extending between said photodetectors, said light beam passing through said stream between said oppositely facing photosensitive surfaces.

* * * * *

UNITED STATES PATENT AND TRADEMARK OFFICE
CERTIFICATE OF CORRECTION

PATENT NO. : 4,917,496

DATED : April 17, 1990

INVENTOR(S) : Holger T. Sommer

It is certified that error appears in the above-identified patent and that said Letters Patent is hereby corrected as shown below:

Column 3, line 9, "surfaces" should be --faces--.

Column 4, line 57, "parent instead" should read --parent. Instead--.

Signed and Sealed this

Seventeenth Day of September, 1991

Attest:

HARRY F. MANBECK, JR.

Attesting Officer

Commissioner of Patents and Trademarks